USshape005329039A

United States Patent [19]

Yanagisawa et al.

[11] Patent Number: 5,329,039

[45] Date of Patent: Jul. 12, 1994

[54] ORGANOSILICON COMPOUND

[75] Inventors: Hideyoshi Yanagisawa, Matsuida; Masaaki Yamaya, Annaka, both of Japan

[73] Assignee: Shin-Etsu Chemical Co., Ltd., Tokyo, Japan

[21] Appl. No.: 50,826

[22] Filed: Apr. 19, 1993

Related U.S. Application Data

[63] Continuation-in-part of Ser. No. 786,018, Oct. 31, 1991, abandoned.

[30] Foreign Application Priority Data

Nov. 1, 1990 [JP] Japan ................... 2-296933

[51] Int. Cl.$^5$ ............................................. C07F 7/18
[52] U.S. Cl. ........................................ 556/485; 556/424
[58] Field of Search .......................... 556/424, 485

[56] References Cited

U.S. PATENT DOCUMENTS

| 4,102,670 | 7/1978 | Foery et al. | 556/485 X |
| 4,254,270 | 3/1981 | Kotzsch et al. | 556/424 X |
| 4,526,996 | 7/1985 | Kilgour et al. | 556/424 X |
| 5,022,922 | 6/1991 | Itagaki et al. | 556/424 X |

FOREIGN PATENT DOCUMENTS

| 0059308 | 1/1982 | European Pat. Off. |
| 0176062 | 9/1985 | European Pat. Off. |
| 0264022 | 9/1987 | European Pat. Off. |
| 0368279 | 11/1989 | European Pat. Off. |

Primary Examiner—Paul F. Shaver
Attorney, Agent, or Firm—Henry T. Burke

[57] ABSTRACT

The novel organosilicon compound of the invention is an alkoxysilane having a silicon-bonded $C_8$ to $C_{14}$ long-chain alkyl group substituted at the $\omega$-position by a bromine atom or an amino ($C_{2-6}$) alkyl-substituted amino group. Synthetic methods of such compounds are described and several examples of the compounds are given with their characterization data. The inventive compound having, in particular, the amino-alkyl-substituted amino group are useful as a surface-treatment agent of a silica filler as a water-resistant reinforcing filler in molding resin compositions.

1 Claim, 2 Drawing Sheets

ORGANOSILICON COMPOUND

BACKGROUND OF THE INVENTION

This is a continuation-in-part application from a co-pending U.S. patent application Ser. No. 07/786,018 filed Oct. 31, 1991 now abandoned.

The present invention relates to a novel organosilicon compound or, more particularly, to a novel alkoxysilane compound having a long-chain alkyl group substituted by a halogen atom or by an N-(aminoalkyl)amino group. The novel organosilicon compound is useful as a priming agent in the adhesive bonding of a variety of organic resins and variety of inorganic materials as well as a modifying agent in composite materials consisting of an organic resin and an inorganic material dispersed therein.

SUMMARY OF THE INVENTION

Thus, the novel organosilicon compound of the invention is an alkoxysilane compound represented by the general formula $$(R^1O)_m Si(CH_3)_{3-m}(R^2—Y), \quad (I)$$

in which $R^1$ is a methyl, ethyl or vinyl group, $R^2$ is a divalent aliphatic hydrocarbon group having 8 to 14 or, in particular, 10 to 14 carbon atoms free from unsaturation, Y is a substituent atom or group selected from the class consisting of a bromine atom and N-aminoalkyl-substituted amino groups, of which the aminoalkyl group has 2 to 6 carbon atoms, and the subscript m is 1, 2 or 3.

DETAILED DESCRIPTION OF THE PREFERRED EMBODIMENTS

Figure 1:
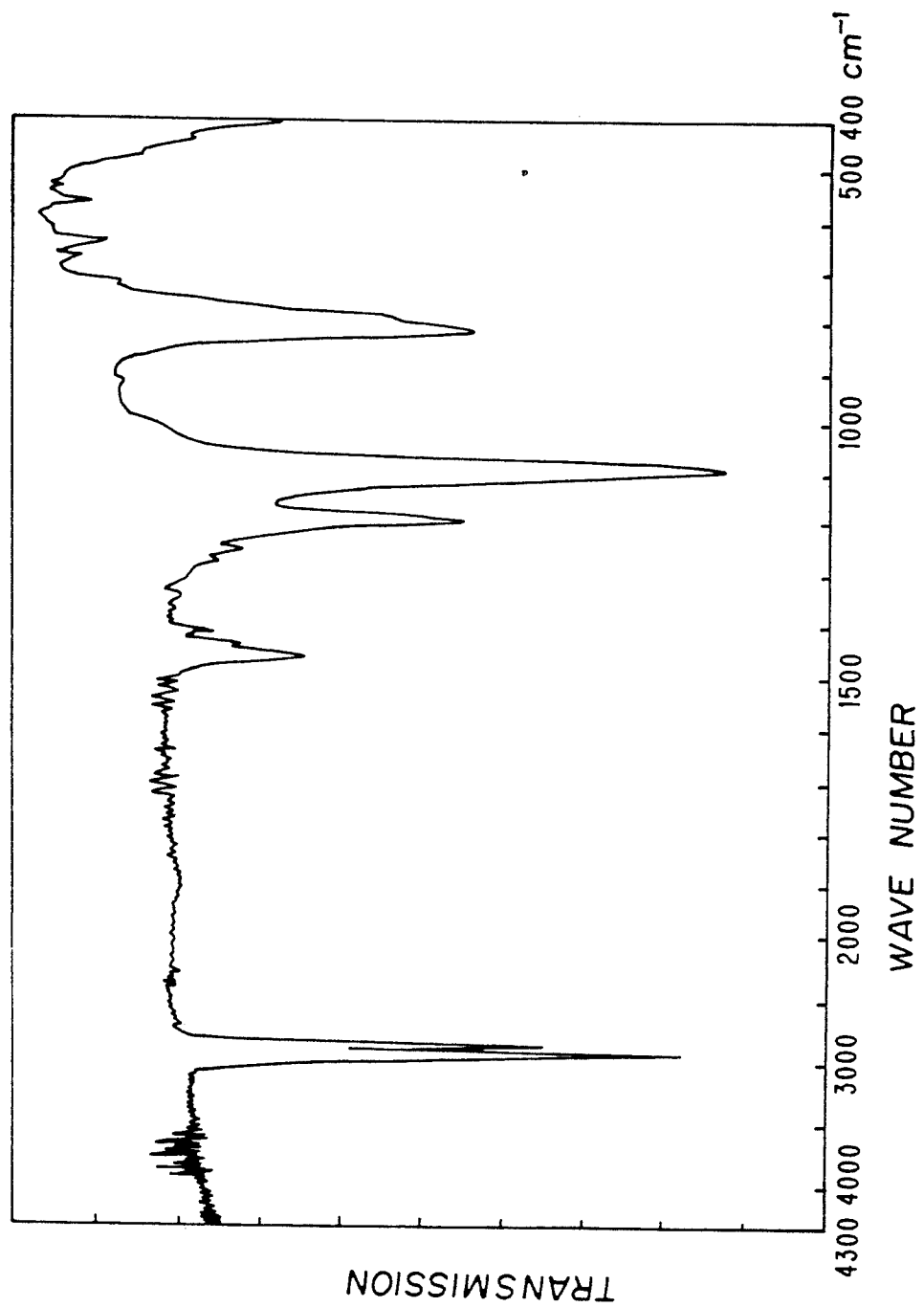
FIG. 1 and FIG. 2 are an infrared absorption spectrum and an $^1$H-NMR spectrum, respectively, of the inventive compound prepared in Example 1.

It is known that alkoxysilanes having an alkyl group substituted by a halogen atom, an amino group or an N-aminoalkyl-substituted amino group are useful as a priming agent in the adhesive bonding between a variety of organic resins and variety of inorganic materials, as a modifying agent in composite materials consisting of an organic resin and an inorganic material dispersed therein, surface-modifying agent of inorganic materials, modifying agent of organic resins, polymerization initiator or polymerization terminator, intermediate for the synthesis of various kinds of other organosilicon compounds, and so on.

Examples of known alkoxysilane compounds of such a class include, for example, 3-chloropropyl trimethoxy silane, 3-chloropropyl triethoxy silane, 3-chloropropyl methyl dimethoxy silane, 3-chloropropyl dimethyl methoxy silane, 3-bromopropyl trimethoxy silane, chloromethyl trimethoxy silane, chloromethyl dimethyl methoxy silane, 2-(4-chloromethylphenyl)ethyl trimethoxy silane, 3-chloro-2-methylpropyl trimethoxy silane and the like as well as 3-aminopropyl trimethoxy silane, 3-aminopropyl triethoxy silane, N-(2-aminoethyl)-3-aminopropyl trimethoxy silane, 3-aminopropyl methyl dimethoxy silane, 3-aminopropyl methyl diethoxy silane, 3-aminopropyl dimethyl methoxy silane, N-(2-aminoethyl)-3-aminopropyl methyl dimethoxy silane, (2-aminoethylaminomethyl)phenethyl trimethoxy silane and the like.

A characteristic feature in these known compounds is that the number of carbon atoms in the saturated divalent aliphatic group linking the halogen atom or the amino group and the silicon atom is always 5 or smaller. The advantages obtained by using these known compounds in the above described applications are not always quite satisfactory so that, directing their attention to this fact as a possible reason for the insufficient performance of these compounds, the inventors have continued extensive investigations to discover more effective organosilicon compounds arriving at the present invention by synthesizing the novel organosilicon compounds defined above.

Namely, the novel organosilicon compound of the invention is represented by the above given general formula (I), in which each symbol has the meaning as defined above. When the symbol Y does not denote a bromine atom, it denotes an aminoalkyl-substituted amino group represented by the general formula $$—NH—(CH_2)_n—NH_2, \quad (II)$$

in which the subscript n is an integer of 2 to 6. In the general formula (I), the symbol $R^1$ denotes a monovalent hydrocarbon group having 1 or 2 carbon atoms exemplified by methyl, ethyl and vinyl groups or, in particular, methyl and ethyl groups. The symbol $R^2$ denotes a divalent aliphatic hydrocarbon group free from unsaturation and having 8 to 14 or, in particular, 10 to 14 carbon atoms exemplified by those groups expressed by the formulas:

—(CH$_2$)$_9$—, —CH(CH$_3$)—(CH$_2$)$_7$—, —(CH$_2$)$_{10}$—, —CH(CH$_3$)—(CH$_2$)$_8$—, —(CH$_2$)$_{11}$13, —CH(CH$_3$)—(CH$_2$)$_9$13 , —(CH$_2$)$_{12}$—, —CH(CH$_3$)—(CH$_2$)$_{10}$—, —(CH$_2$)$_{13}$—, —CH(CH$_3$)—(CH$_2$)$_{11}$—, —(CH$_2$)$_{14}$— and —CH(CH$_3$)—(CH$_2$)$_{12}$—.

Examples of the inventive novel organosilicon compounds include those expressed by the following formulas:

(CH$_3$O)$_3$Si(CH$_2$)$_8$Br, (CH$_3$O)$_3$Si(CH$_2$)$_{10}$Br,
(CH$_3$O)$_3$Si(CH$_2$)$_8$Br, (CH$_3$CH$_2$O)$_3$Si(CH$_2$)$_{10}$Br,
(CH$_3$CH$_2$O)$_3$Si(CH$_2$)$_8$Br, (CH$_3$CH$_2$O)$_3$Si(CH$_2$)$_{14}$Br,
(CH$_3$CH$_2$O)$_3$Si(CH$_2$)$_{12}$Br, (CH$_3$CH$_2$O)$_3$Si(CH$_2$)$_{14}$Br,
(CH$_3$CH$_2$O)$_3$(CH$_3$)Si(CH$_2$)$_{10}$Br,
(CH$_3$CH$_2$O)$_3$CH$_3$)Si(CH$_2$)$_8$Br,
(CH$_3$CH$_2$O)(CH$_3$)$_2$Si(CH$_2$)$_{10}$Br,
(CH$_3$O)$_3$Si(CH$_2$)$_{10}$NH(CH$_2$)$_2$NH$_2$,
(CH$_3$O)$_3$Si(CH$_2$)$_{10}$NH(CH$_2$)$_4$NH$_2$,
(CH$_3$O)$_3$Si(CH$_2$)$_{10}$NH(CH$_2$)$_6$NH$_2$,
(CH$_3$O)$_2$(CH$_3$)Si(CH$_2$)$_{10}$NH(CH$_2$)$_2$NH$_2$,
(CH$_3$O)$_2$(CH$_3$)Si(CH$_2$)$_{10}$NH(CH$_2$)$_4$NH$_2$,
(CH$_3$O)$_2$(CH$_3$)Si(CH$_2$)$_{10}$NH(CH$_2$)$_6$NH$_2$,
(CH$_3$O)(CH$_3$)$_2$Si(CH$_2$)$_{10}$NH(CH$_2$)$_2$NH$_2$,
(CH$_3$O)(CH$_3$)$_2$Si(CH$_2$)$_{10}$NH(CH$_2$)$_4$NH$_2$,
(CH$_3$O)(CH$_3$)$_2$Si(CH$_2$)$_{10}$NH(CH$_2$)$_6$NH$_2$,
(CH$_3$O)$_3$Si(CH$_2$)$_{14}$NH(CH$_2$)$_2$NH$_2$,
(CH$_3$O)$_3$Si(CH$_2$)$_{14}$NH(CH$_2$)$_4$NH$_2$,
(CH$_3$O)$_3$Si(CH$_2$)$_{14}$NH(CH$_2$)$_6$NH$_2$,
(CH$_3$O)$_2$(CH$_3$)Si(CH$_2$)$_{14}$NH(CH$_2$)$_2$NH$_2$,
(CH$_3$O)$_2$(CH$_3$)Si(CH$_2$)$_{14}$NH(CH$_2$)$_6$NH$_2$,
(CH$_3$O)(CH$_3$)$_2$Si(CH$_2$)$_{14}$NH(CH$_2$)$_2$NH$_2$,
(CH$_3$O)(CH$_3$)$_2$Si(CH$_2$)$_{14}$NH(CH$_2$)$_6$NH$_2$,
(CH$_3$O)$_3$Si(CH$_2$)$_8$NH(CH$_2$)$_2$NH$_2$,
(CH$_3$O)$_3$Si(CH$_2$)$_8$NH(CH$_2$)$_6$NH$_2$, $(CH_3O)_2(CH_3)Si(CH_2)_8NH(CH_2)_2NH_2$,
$(CH_3O)_2(CH_3)Si(CH_2)_8NH(CH_2)_6NH_2$,
$(CH_3O)(CH_3)_2Si(CH_2)_8NH(CH_2)_2NH_2$,
$(CH_3O)(CH_3)_2Si(CH_2)_8NH(CH_2)_6NH_2$,
$(CH_3O)_3Si(CH_2)_{12}NH(CH_2)_2NH_2$,
$(CH_3O)_3Si(CH_2)_{12}NH(CH_2)_6NH_2$,
$(CH_3O)_2(CH_3)Si(CH_2)_{12}NH(CH_2)_2NH_2$,
$(CH_3O)_2(CH_3)Si(CH_2)_{12}NH(CH_2)_6NH_2$,
$(CH_3O)(CH_3)_2Si(CH_2)_{12}NH(CH_2)_2NH_2$,
$(CH_3O)(CH_3)_2Si(CH_2)_{12}NH(CH_2)_6NH_2$,
$(CH_3O)(CH_3)_2Si(CH_2)_{14}NH(CH_2)_4NH_2$,
$(CH_3CH_2O)_3Si(CH_2)_{10}NH(CH_2)_2NH_2$,
$(CH_3CH_2O)_3Si(CH_2)_{10}NH(CH_2)_6NH_2$,
$(CH_3CH_2O)_2(CH_3)Si(CH_2)_{10}NH(CH_2)_2NH_2$,
$(CH_3CH_2O)(CH_3)_2Si(CH_2)_{10}NH(CH_2)_2NH_2$,
$(CH_3CH_2O)_3Si(CH_2)_6NH(CH_2)_2NH_2$,
$(CH_3CH_2O)_3Si(CH_2)_{14}NH(CH_2)_2NH_2$,
$(CH_3CH_2O)_2(CH_3)Si(CH_2)_{14}NH(CH_2)_6NH_2$,
$(CH_3CH_2O)_3Si(CH_2)_8NH(CH_2)_2NH_2$, and
$(CH_3CH_2O)_3Si(CH_2)_{12}NH(CH_2)_2NH_2$.

Following is a description of the method for the synthetic preparation of the above defined and exemplified compounds of the invention.

Thus, the starting organosilicon compound for the synthesis thereof is an alkoxy hydrogensilane represented by the general formula $$(R^1O)_m SiH(CH_3)_{3-m}, \quad (III)$$

in which each symbol has the same meaning as defined before. This compound is subjected to a hydrosilation reaction with an ethylenically α-unsaturated compound represented by the general formula $$CH_2 = CH-R^3-Y, \quad (IV)$$

in which Y has the same meaning as defined before and $R^3$ is an aliphatic divalent hydrocarbon group free from unsaturation having 6 to 12 carbon atoms, in the presence of a catalytic amount of a catalyst compound which can be a compound of a transition metal of the VIIIth group of the Periodic Table such as platinum, rhodium, ruthenium, nickel, cobalt and the like or, in particular, platinum. The reaction can be performed by mixing the reactants and the catalyst and heating the mixture at a temperature of 30 to 150° C. for 30 minutes to 18 hours.

The reaction mixture can be diluted, if necessary, with an organic solvent which is, though not particularly limitative, exemplified by aromatic hydrocarbon solvents such as benzene, toluene and xylene, aliphatic hydrocarbon solvents such as pentane, hexane, heptane, octane, nonane and decane, ethers such as diethyl ether, tetrahydrofuran and dioxane, ketones such as acetone, methyl ethyl ketone and methyl isobutyl ketone, alcohols such as methyl alcohol and ethyl alcohol, halogenated aliphatic hydrocarbon solvents such as perchloroethane, perchloroethylene, trichloroethane, chloroform and carbon tetrachloride, amides such as dimethylformamide, esters such as methyl acetate, ethyl acetate and isopropyl acetate, and so on.

Alternatively, the compound of the invention can be prepared by first subjecting a chloro hydrogensilane compound represented by the general formula $$Cl_m SiH(CH_3)_{3-m}, \quad (V)$$

in which the symbol m has the same meaning as defined above, to the hydrosilation reaction with the unsaturated compound of the formula (IV) given above under substantially the same reaction conditions described above to give a compound of the formula $$CL_m Si(CH_3)_{3-m}(CH_2-CH_2-R^3-Y), \quad (VI)$$

ps which is then subjected to a dehydrochlorination condensation reaction with an alcohol represented by the general formula $$R^1OH,$$

in which $R^1$ has the same meaning as defined above, by heating the reaction mixture at a temperature of 20 to 150° C. for 30 minutes to 18 hours in the presence of an acid acceptor. The reactions of this route of synthesis can be performed by diluting the reactants with an organic solvent which can be exemplified by those given as the examples of the solvent to be used in the first route of synthesis.

The above mentioned acid acceptor of the hydrogen chloride is exemplified by tertiary amines such as triethyl amine, trimethyl amine, amino compounds such as urea and the like and alkali alcoholares such as sodium methoxide and sodium ethoxide.

When the substituent group denoted by Y in the inventive compound is an aminoalkyl-substituted amino group of the formula $-NH-(CH_2)_n-NH_2$ the compound can be synthesized in a synthetic route described below. Thus, a compound represented by the general formula $$(R^1O)_m Si(CH_3)_{3-m}(R^2-X), \quad (VII)$$

in which X is an atom of halogen or, in particular, chlorine, is synthesized in the same method as or similar method to the above described method and this compound is then subjected to a dehydrohalogenation reaction with an alkyl-enediimaine compound represented by the general formula $$NH_2-(CH_2)_n-NH_2, \quad (VIII)$$

in which n is an integer of 2 to 6. The molar ratio of the silane compound of the formula (VII) and the alkylenediamine of the formula (VIII) should be at least 0.5 or, preferably, at least 1.0. The reaction is usually complete within 30 minutes to 18 hours at a temperature of 50 to 150° C.

The above mentioned dehydrohalogenation reaction should be performed in the presence of an acid acceptor. Although any of the acceptor compounds of which examples are given earlier serves for the purpose, it is sometimes convenient to use the alkylenediamine compound of the formula (VIII) in an excess amount so that the excess of this diamine compound may serve as the acid acceptor. It is of course that this dehydrohalogenation reaction is performed by diluting the reactants with an organic solvent which can be exemplified by those previously given as the examples of the solvent used in the synthesis of the compound of which Y is a bromine atom.

In the following, examples are given for the synthesis and characterization of the novel alkoxysilane compounds according to the invention.

EXAMPLE 1

Into a flask of 1 liter capacity equipped with a stirrer, thermometer, reflux condenser and dropping funnel were introduced 219 g (1 mole) of 10-bromo-1-decene and 0.1 g of an isopropyl alcohol solution of chloroplatinic acid in a concentration of 2% by weight as platinum. Then, 128.7 g (0.95 mole) of trichlorosilane were gradually added dropwise into the mixture in the flask under a stream of nitrogen gas at such a rate that the temperature of the reaction mixture in the flask was kept at a temperature in the range from 45 to 60° C. After completion of the dropwise addition of the trichlorosilane, the reaction mixture was further agitated for two hours at 60° C.

In the next place, 180 g (3 moles) of urea were added to the reaction mixture and then 128 g (4 moles) of methyl alcohol were gradually added thereto dropwise at such a rate that the temperature of the reaction mixture was kept at 50 to 65° C. After completion of the dropwise addition methyl alcohol, the reaction mixture was further agitated for 2 hours at 60° C.

The reaction mixture was separated into two layers upon standing do that the lower layer was discarded and the organic solution in the upper layer was taken and concentrated by evaporation at 80° C. under a pressure of 10 mmHg so that 330 g of a clear, light brown liquid was obtained as a crude product.

The above obtained crude liquid product was subjected to purification by distillation to obtain 276 g of a fraction boiling at 160 to 162° C. under a pressure of 3 mmHg as a clear, colorless liquid. This liquid product could be identified to be 10-bromodecyl trimethoxy silane from the analytical results shown below obtained by the infrared absorption spectrophotometric analysis, NMR spectrometric analysis and elementary analysis. The purity of the product relative to the compound was 98.3% according to the result of the gas chromatographic analysis. The above mentioned yield of the compound corresponds to 85.2% of the theoretical value.

Result of elementary analysis

|  | C | H | Si | Br |
|---|---|---|---|---|
| Calculated, % | 45.74 | 8.56 | 8.23 | 23.41 |
| Found, % | 45.51 | 8.47 | 8.34 | 23.56 |

Figure 2:
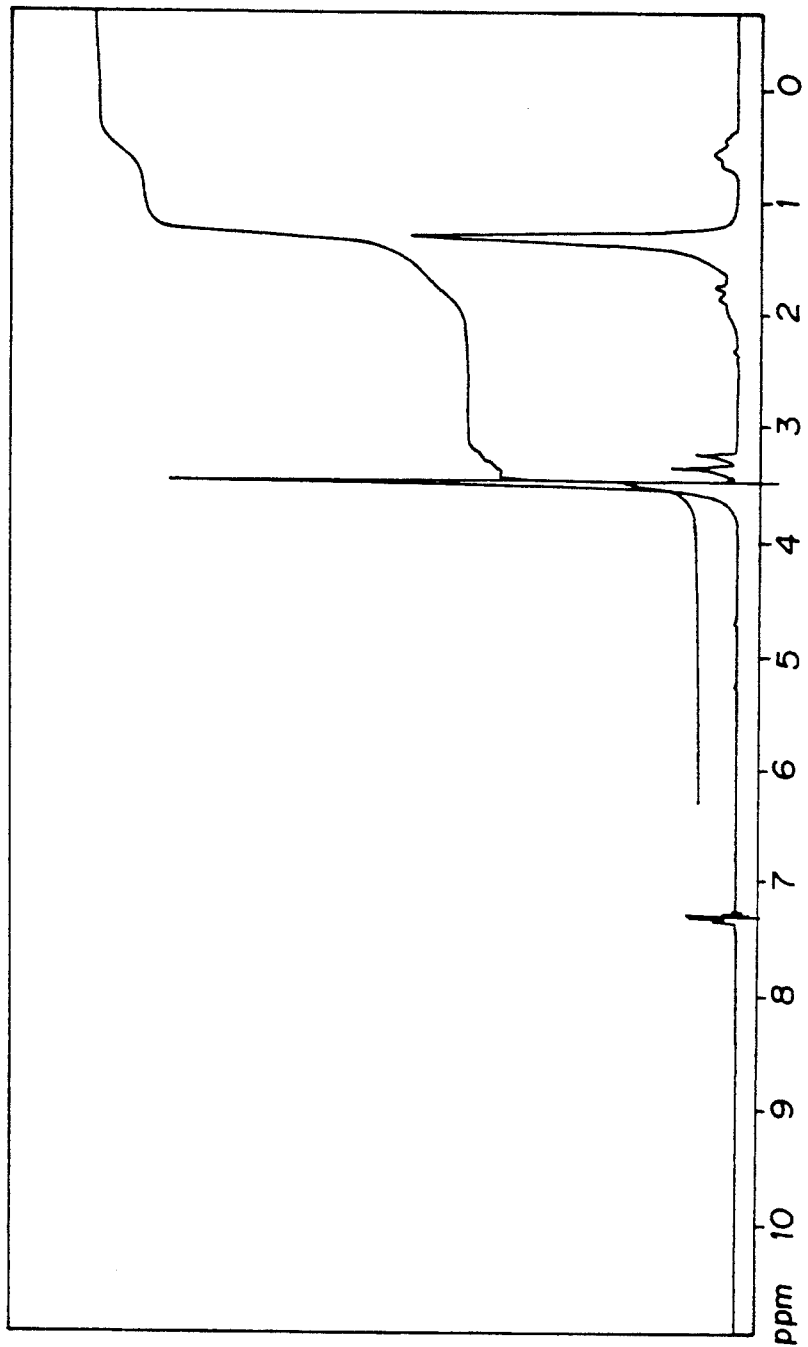

Infrared absorption spectrum (see FIG. 1):
1082 and 1192 cm$^{-1}$: Si—O—C
1462, 2841 and 2946 cm$^1$:C—H
563 cm$^{-1}$: C—Br
spectrum (see FIG. 2)
(internal standard, benzene, $\delta=7.24$ ppm)
$\delta=3.45$ ppm (s,9H):Si—O—CH$_3$
$\delta=0.30$–0.70 ppm (m, 2H): Si—CH$_2$—
$\delta=1.10$–1.52 ppm (M, 14H):Si—CH$_2$—(CH$_2$)$_7$—CH$_2$—Br
$\delta=1.52$–2.10 ppm (m, 2H):CH$_2$—CH$_2$—Br
$\delta=3.33$ ppm (t, 2H):CH$_2$—CH$_2$—Br

EXAMPLE 2.

Into a flask of 2 liter capacity equipped with a stirrer, thermometer, reflux condenser and dropping funnel were introduced 540 g (9 moles) of ethylenediamine and then 341.4 g (1 mole) of 10-bromodecyl trimethoxy silane were gradually added dropwise into the flask under a stream of nitrogen gas at such a rate that the temperature of the reaction mixture in the flask was kept at a temperature in the range from 70 to 80° C. After completion of the dropwise addition of the silane, the reaction mixture was further agitated for five hours at 80° C.

In the next place, 193 g of a methyl alcohol solution containing 1 mole of sodium methoxide were added dropwise to the reaction mixture at 60° C. followed by continued agitation of the mixture at 60° C. for 1 hour.

The reaction mixture was filtered to remove the precipitates of sodium bromide formed by the dehydrobromination reaction and the liltrate was concentrated by evaporation at 120° C. under a pressure of 3 mmHg so that 242.4 g of a clear, brown liquid were obtained.

The above obtained liquid product could be identified to be N-(2-aminoethyl)-10-aminodecyl trimethoxy silane from the analytical results shown below obtained by the infrared absorption spectrophotometric analysis, NMR spectrometric analysis and elementary analysis. The amine equivalent of this liquid product as determined by the neutralization titration with hydrochloric acid was 161.0 g/mole which was in good coincidence with the theoretical value of 160.75 g/mole. The above mentioned yield of this product compound corresponds to 75.4% of the theoretical value.

Result of elementary analysis

|  | C | H | Si | N |
|---|---|---|---|---|
| Calculated, % | 56.21 | 11.32 | 8.76 | 8.74 |
| Found, % | 56.09 | 11.13 | 8.88 | 8.82 |

Infrared absorption spectrum:
1090, 1192 and 2854 cm$^{-1}$:Si—O—CH$_3$;
1471, 2854 and 2924 cm$^{-1}$:C—H;
1597 cm$^{-1}$:C—N;
3319 cm$^{-1}$:N—H
$^1$H—NMR spectrum
(internal standard, benzene, $\delta=7.24$ ppm);
$\delta=3.48$ ppm (s 9H):Si—O—CH;
$\delta=0.25$–0.75 ppm (m, 2H):Si—CH$_2$—(CH$_2$)$_8$—CH$_2$;
$\delta=0.75$ -1.75 ppm (m, 19H):Si—CH$_2$—(CH$_2$)$_8$—CH$_2$; NH—(CH$_2$—)$_2$—NH$_2$;
$=2.25$-2.90 ppm (m, 6H): Si—CH$_2$—(CH$_2$)$_8$—CH$_2$—NH—(CH$_2$)$_2$—NH$_2$

EXAMPLE 3

Reactivity of 10-bromodecyl trimethoxy silane

Into a four-necked flask of 1 liter capacity equipped with a thermometer, Dimroth condenser, stirrer and dropping funnel were introduced 200.0 g of dimethylformamide and 124.0 g (1 mole) of potassium methacrylate to form a mixture into which 340.9 g (1 mole) of 10-bromodecyl trimethoxy silane were gradually added dropwise while keeping the mixture in the flask at 60° C. After completion of the dropwise addition of the silane to the flask, the reaction mixture was further agitated for 5 hours at 60° C. to complete the reaction.

After the end of the above mentioned reaction time, the reaction mixture was filtered to remove the precipitates of the salt which was potassium bromide and the liltrate was subjected to the gas chromatographic analysis to find disappearance of the 10-bromodecyl trimethoxy silane as the starting reactant. The liltrate was purified by distillation to give 214.9 g of a clear and colorless liquid as the principal fraction. This liquid product could be identified to be 10-methacryloxydecyl trimethoxy silane from the results of the NMR analysis, infrared absorption spectrophotometric analysis and mass spectrometric analysis. The above mentioned yield of the product corresponds to 62% of the theoretical value.

For comparison, the same experimental procedure for synthesis as above was repeated excepting replacement of the 10-bromodecyl trimethoxy silane with the same molar amount of 3-bromopropyl trimethoxy silane. The result was that 162.9 g of a clear and colorless liquid product was obtained, which could be identified to be 3-methacryloxypropyl trimethoxy silane. The above mentioned yield of this product corresponds to 66% of the theoretical value.

For further comparison, the same experimental procedure as above was repeated excepting replacement of the 10-bromodecyl trimethoxy silane with the same molar amount of 10-chlorodecyl trimethoxy silane or 3-chloropropyl trimethoxy silane. The result was that the amount of the salt precipitated in the reaction mixture was very small even after a prolonged reaction time at 60° C. indicating that the reaction had little proceeded between the reactants. The gas chromatographic analysis of the liquid reaction mixture also indicated that the amount of the starting silane compound had been little decreased.

APPLICATION EXAMPLE

A surface-treated silica filler was prepared by uniformly compounding 500 parts by weight of a silica filler, 20 parts by weight of deionized water, 475 parts by weight of methyl alcohol and 5 parts by weight of N-(2-aminoethyl)-10-aminodecyl trimethoxy silane prepared in example 2 described above followed by drying at 100° C. for 5 hours under reduced pressure.

A molding resin composition was prepared by uniformly blending, on a two-roller mill, 36.07 parts by weight of a phenolic resin, 63.93 parts by weight of an epoxy resin, 1.0 part by weight of a carnauba wax, 0.7 part by weight of triphenyl phosphine and 300 parts by weight of the above prepared surface-treated silica filler and the molding composition was shaped by injection molding at 175° C. into test pieces each having dimensions of 80 mm by 10 mm by 4 mm.

The test pieces were subjected to a pressure-cooker test in water at 120° C. (2.1 atmospheres) for 40 hours to cause absorption of water. The test pieces after water absorption was subjected to the determination of the flexural strength to give a value of 12.1 kgf/mm$^2$.

The same experiment as above was repeated by replacing the N-(2-aminoethyl)-10-aminodecyl trimethoxy silane with the same amount of methyl diethoxy N-(6-aminohexyl)-6-aminohexyl silane, dimethyl methoxy N-(4-aminobutyl)-14-aminotetradecyl silane or N-(2-aminoethyl)-3-aminopropyl trimethoxy silane. The test specimens prepared by using these alkoxy silanes had a flexural strength of 10.7 kgf/mm$^2$, 11.2 kgf/mm$^2$ and 8.3 kgf/mm$^2$, respectively.

What is claimed is:
1. 10-Bromodecyl trimethoxy silane.

* * * * *